(12) United States Patent
Desfougeres et al.

(10) Patent No.: US 9,458,469 B2
(45) Date of Patent: Oct. 4, 2016

(54) METHOD FOR OBTAINING IMPROVED STRAINS OF YEAST

(71) Applicant: LESAFFRE ET COMPAGNIE, Paris (FR)

(72) Inventors: Thomas Desfougeres, Neuville en Ferrain (FR); Georges Pignede, Marcq-en-Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 14/403,574

(22) PCT Filed: May 27, 2013

(86) PCT No.: PCT/FR2013/051160
§ 371 (c)(1),
(2) Date: Nov. 24, 2014

(87) PCT Pub. No.: WO2013/178918
PCT Pub. Date: Dec. 5, 2013

(65) Prior Publication Data
US 2015/0284730 A1    Oct. 8, 2015

(30) Foreign Application Priority Data
Jun. 1, 2012 (FR) ..................... 12 55118

(51) Int. Cl.
| | | |
|---|---|---|
| *C12N 15/81* | (2006.01) | |
| *C12R 1/865* | (2006.01) | |
| *C07K 14/395* | (2006.01) | |
| *C12N 15/04* | (2006.01) | |
| *C12N 15/90* | (2006.01) | |

(52) U.S. Cl.
CPC ............ *C12N 15/81* (2013.01); *C07K 14/395* (2013.01); *C12N 15/04* (2013.01); *C12N 15/902* (2013.01); *C12N 15/905* (2013.01); *C12R 1/865* (2013.01)

(58) Field of Classification Search
None
See application file for complete search history.

(56) References Cited

U.S. PATENT DOCUMENTS

| | | | |
|---|---|---|---|
| 2012/0202251 A1* | 8/2012 | Cornish et al. ............ | 435/91.41 |
| 2014/0099719 A1* | 4/2014 | Buonamassa ............ | C12N 7/00 |
| | | | 435/471 |

FOREIGN PATENT DOCUMENTS

| | | |
|---|---|---|
| FR | 2 679 249 | 1/1993 |
| WO | 02/29009 | 4/2002 |
| WO | 2009/112940 | 9/2009 |
| WO | 2011/128552 | 10/2011 |

OTHER PUBLICATIONS

International Search Report dated Jul. 31, 2013, which issued during prosecution of International Application No. PCT/FR2013/051160.
Yamane, et al. "Region specificity of chromosome III on gene expression in the yeast *Saccharomyces cerevisiae* " Journal of General and Applied Microbiology, Aug. 1998, 44(4):275-281.

* cited by examiner

*Primary Examiner* — Jim Ketter
(74) *Attorney, Agent, or Firm* — Vedder Price P.C.; Thomas J. Kowalski; Deborah L. Lu (57) ABSTRACT

The present invention relates to a method for obtaining improved strains of yeast by integrating at least one gene of interest in a region linked to a sex expression locus, followed by cross-breeding. The present invention also relates to gene integration cassettes and to vectors that can be used in the context of said method. The present invention also relates to improved strains of yeast obtained by the above method, the derived strains of yeast and the yeasts obtained by culturing said strains of yeast.

29 Claims, 1 Drawing Sheet

SEQUENCE LISTING

```
<160> NUMBER OF SEQ ID NOS: 4

<210> SEQ ID NO 1
<211> LENGTH: 34
<212> TYPE: DNA
<213> ORGANISM: Unknown
<220> FEATURE:
<223> OTHER INFORMATION: Description of Unknown: Bacteriophage P1
      oligonucleotide

<400> SEQUENCE: 1
ataacttcgt ataatgtatg ctatacgaag ttat                              34

<210> SEQ ID NO 2
<211> LENGTH: 23
<212> TYPE: DNA
<213> ORGANISM: Saccharomyces cerevisiae

<400> SEQUENCE: 2
agtcacatca agatcgttta tgg                                          23

<210> SEQ ID NO 3
<211> LENGTH: 23
<212> TYPE: DNA
<213> ORGANISM: Saccharomyces cerevisiae

<400> SEQUENCE: 3
gcacggaata tgggactact tcg                                          23

<210> SEQ ID NO 4
<211> LENGTH: 23
<212> TYPE: DNA
<213> ORGANISM: Saccharomyces cerevisiae

<400> SEQUENCE: 4
actccacttc aagtaagagt ttg                                          23
```

METHOD FOR OBTAINING IMPROVED STRAINS OF YEAST

RELATED APPLICATIONS

The present application is filed pursuant to 35 U.S.C. §371 as a U.S. National Phase application of International Patent Application No. PCT/FR2013/051160, which was filed on May 27, 2013, claiming the benefit of priority to French Patent Application No. FR 1255118 filed on Jun. 1, 2012. The entire content of each of the aforementioned patent applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 3, 2015, is named 44980.00.2015_SL.txt and is 1,019 bytes in size.

TECHNICAL FIELD

The present invention relates to the technologies for obtaining improved strains of yeast.

TECHNOLOGICAL BACKGROUND

As a result of the progress in molecular biology, in cell biology and in genetics, many tools are now available for modifying a cell, whether it is a prokaryotic cell or a eukaryotic cell such as yeast.

For example, it is possible to obtain a cell which produces or uses new compounds, or else to improve the properties of a cell, by using gene modification techniques, whether by integration, deletion or disruption of DNA sequences, or by site-directed or random mutagenesis.

Those skilled in the art also have available older techniques such as crossing techniques.

Those skilled in the art can also combine these techniques, for instance carrying out a mutagenesis on a genetically modified strain of yeast, or genetically modifying a strain of yeast obtained by crossing.

However, those skilled in the art are sometimes limited by the laboriousness, the time required and the lack of efficiency of the known techniques for obtaining the desired improved cell.

The modification of a yeast strain makes it possible to obtain yeasts with different or improved properties, which can be used in many possible applications, among which breadmaking, the food industry, health, the production of compounds, for example alcohol, the production of yeast extracts.

The crossing of yeast strains is a technique which is widely used, but which often requires optimizations in order to increase the chances of obtaining the desired yeast strain, for example the selection of segregants on the basis of particular properties.

However, the lack of efficiency of the crossing of yeast strains is far from being solved for all situations. For example, it is difficult to envision using the crossing technique starting from a yeast strain which has undergone several genetic modifications. This is because the probability of obtaining segregants having all the genetic modifications of the starting strain decreases with the number of genetic modifications.

Thus, there is still a need to provide novel methods for obtaining improved strains of yeast, these methods being faster and simple to carry out and allowing a more efficient selection of the yeast strains having the desired improvements.

SUMMARY OF THE INVENTION

A first object of the invention relates to a gene integration cassette comprising:
at least one expression cassette comprising a gene of interest framed by a promoter and a terminator,
two recombination sequences which are homologs of a region linked to a sex type expression locus and which frame said expression cassettes.

A second object of the invention relates to a vector comprising a gene integration cassette as defined above.

A third object of the invention relates to a yeast strain comprising at least two genes of interest integrated into a region linked to the same-sex-type expression locus, preferably transformed with a gene integration cassette as defined above or a vector as defined above.

A fourth object of the invention relates to a method for obtaining an improved strain of yeast by integrating at least one gene of interest and then crossing, comprising the steps of:
selecting a yeast strain X which is heterothallic and heterozygous at the level of the sex type expression locus,
integrating, in the genome of said yeast strain X, at least one gene of interest into a region linked to a sex type expression locus, so as to obtain a genetically modified yeast strain X,
crossing the genetically modified yeast strain X with a yeast strain Y, so as to obtain a hybrid.

A fifth object of the invention relates to an improved strain of yeast which can be obtained by means of the method for obtaining an improved strain of yeast as defined above.

A sixth object of the invention relates to a yeast strain derived from an improved strain of yeast as defined above, said derived strain of yeast comprising said gene(s) of interest of the yeast strain X.

A seventh object of the invention relates to a yeast obtained by culturing an improved strain of yeast as defined above or a derived strain of yeast as defined above.

An eighth object of the invention relates to the use of a region linked to the sex type expression locus, for integrating at least one gene of interest into a yeast strain intended to be crossed with a yeast strain.

DESCRIPTION OF THE FIGURES

The expression cassette comprises:
- an expression cassette comprising the STL1 gene of interest framed by the pADH1 promoter (P) and the tCYC1 terminator (T).
- two lox sequences which frame an expression cassette, said expression cassette comprising a kanamycin selectable marker (M KAN) framed by a promoter (PM) and a terminator (TM),
- two recombination sequences (SR-BUD5 and SR-alpha2) which are homologs respectively of the 5' end of the BUD5 gene and of the 3' end of the alpha2 gene.

DETAILED DESCRIPTION OF THE INVENTION

The object of the present invention is thus to provide a novel method which is fast, efficient and simple to carry out and which makes it possible to obtain improved strains of yeast.

Entirely originally, the inventors have demonstrated that it is possible to efficiently select the segregants of a genetically modified yeast strain by integrating the genetic modification(s) into a region genetically linked to a locus responsible for the sex type.

Thus, after sporulation of the genetically modified yeast strain, the genetic modification(s) segregate(s) jointly and are all located in a segregant of the corresponding sex type.

The original method according to the invention is all the more advantageous since it is applicable to any gene, for any type of possible improvement and to any yeast strain which has a haplodiplontic cycle.

A haplodiplontic cycle is a reproductive cycle which alternates a haploid phase and diploid phase and during which the organism under consideration can multiply by mitosis both in the haploid state and in the diploid state.

A yeast strain which has a haplodiplontic cycle is subsequently referred to as haplodiplontic yeast strain.

Therefore, the method according to the invention is not limited to one or more particular genes of interest.

The expression "yeast strain" denotes a relatively homogeneous population of yeast cells.

A yeast strain is obtained from the isolation of a clone, a clone being a population of cells that has been obtained from a single yeast cell.

The method according to the invention can be used for improving any haplodiplontic yeast strain.

A preferred haplodiplontic yeast strain according to the invention is a hemiascomycete or a strain of the *Schizosaccharomyces* genus.

A hemiascomycete haplodiplontic yeast strain which can be used in the context of the invention is, for example, a yeast strain of the *Saccharomyces, Candida. Pichia* or *Yarrowia* genus.

A yeast strain of the *Saccharomyces* genus used in the context of the invention is, for example, chosen from *Saccharomyces bailii, Saccharomyces boulardii, Saccharomyces carlsbergensis, Saccharomyces cerevisiae, Saccharomyces delbrueckii, Saccharomyces exiguus, Saccharomyces fermentati, Saccharomyces florentinus, Saccharomyces fragilis, Saccharomyces fructuum, Saccharomyces kefir, Saccharomyces kluyveri, Saccharomyces rosei, Saccharomyces steineri* and *Saccharomyces uvarum*.

A yeast strain of the *Candida* genus used in the context of the invention is, for example, chosen from *Candida albicans* and *Candida glabrata*.

A yeast strain of the *Pichia* genus used in the context of the invention is, for example, chosen from *Pichia anomola, Pichia heedii, Pichia guilliermondii, Pichia kluyveri, Pichia membranifaciens, Pichia norvegensis, Pichia ohmeri, Pichia pastoris, Pichia subpelliculosa* and *Pichia stipitis*.

A yeast strain of the *Yarrowia* genus used in the context of the invention is, for example, *Yarrowia lipolytica*.

A yeast strain used in the context of the invention is, for example, a yeast strain phylogenetically close to *Yarrowia lipolytica*, for example *Candida deformans* or *Candida gali*.

A yeast strain of the *Schizosaccharomyces* genus used in the context of the invention is, for example, *Schizosaccharomyces pombe*.

The sex type expression locus is used here to denote any expressed locus responsible for the sex type in a haploid yeast strain and which is not expressed in the corresponding diploid yeast strain.

An expressed locus responsible for the sex type therefore corresponds to a region of the genome of a yeast strain which has everything required to express a sex type in said yeast strain in a haploid state and which is not expressed in the corresponding diploid yeast strain.

The use of the term "expression locus" is important, since there is in some yeast strains one or more loci identical to the sex type expression locus, but which are silent.

A sex type expression locus can comprise several genes.

A sex expression locus generally comprises two alleles which each define a sex type, also called haplotype.

The cells of a given sex type can fertilize only the cells of the other sex type. The cells of a given sex type are herein described as being of sex type compatible with the cells of the other sex type.

The term "allele" is therefore used broadly, since a sex type expression locus generally comprises several genes.

The sex type expression locus thus encompasses herein a MAT (Mating-type) locus and an MTL (Mating-type-like) locus.

For example, in a *Saccharomyces* yeast strain, the sex type expression locus is a MAT locus which comprises two alleles: MATa and MATalpha.

The *Saccharomyces* yeast strain also comprises silent copies of the MATa and MATalpha alleles which are also respectively called HMRa and HMRalpha.

In a *Schizosaccharomyces* yeast strain, the sex type expression locus is a MAT locus which comprises two alleles: MAT1-P and MAT1-M.

The *Schizosaccharomyces* yeast strain also comprises silent copies of the MAT P and MAT M alleles which are also respectively called mat2-P and mat-2-M.

In a *Candida* yeast strain, the sex type expression locus is an MTL (Mating-Type-Like) locus.

The *Candida* yeast strain generally has an MTLa allele and an MTLalpha allele.

In one preferred embodiment, the sex type expression locus is the *Saccharomyces* MAT locus.

The *Saccharomyces cerevisiae* MAT locus is, for example, located on chromosome III, on the large arm of said chromosome, between positions 190 000 base pairs and 210 000 base pairs starting from the telomere of the short arm.

The MATalpha allele of the *Saccharomyces cerevisiae* yeast strain comprises the alpha1 gene and the alpha2 gene.

The MATa allele of the *Saccharomyces cerevisiae* yeast strain comprises the a1 gene and the a2 gene.

The genetic modification(s) of the improved strain of yeast according to the invention can be obtained by means of a gene integration cassette according to the invention.

An object of the present invention is thus a gene integration cassette comprising:
- at least one expression cassette comprising a gene of interest framed by a promoter and a terminator,
- two recombination sequences which are homologs of a region linked to a sex type expression locus and which frame said expression cassette(s).

The term "gene" denotes herein a coding DNA sequence, also called "open reading frame".

As indicated above, the gene of interest may be any coding DNA sequence that it is desired to express in a yeast strain.

A promoter is a DNA sequence required for the initiation and the control of transcription.

The promoter is preferably a promoter of the yeast strain into which the gene integration cassette is intended to be integrated.

For example, the promoter is a *Saccharomyces* promoter chosen from pADH1, pTDH3, pPGK1, pADH2, pPDC2, pPMA1 and pGPD1.

The term "pX" denotes the promoter of the gene X.

A terminator is a DNA sequence required for the termination of transcription.

The terminator is preferably a terminator of the yeast strain into which the gene integration cassette is intended to be integrated.

For example, the terminator is a *Saccharomyces* terminator chosen from tCYC1, tTAL1 and tTKL1.

The term "tX" denotes the terminator of the gene X.

The sex type expression locus is as defined above.

The sex type expression locus is, for example, a MAT locus or an MTL locus.

The two recombination sequences which are homologs of a region linked to a sex type expression locus are such that they allow the integration of said expression cassette(s) into a region linked to the sex type expression locus.

Each of these recombination sequences is therefore a homolog of a region linked to a sex type expression locus.

The two recombination sequences may or may not be homologs of adjacent sequences of the region linked to a sex type expression locus.

If the two recombination sequences are not homologs of adjacent sequences, the DNA sequence included between the regions homologous to the recombination sequences is excised at the moment the gene integration cassette is integrated into the yeast strain.

The two recombination sequences are such that the function of the sex type expression locus is not impaired after integration of the gene integration cassette into the genome of the yeast strain, so that the segregants produced by sporulation of said yeast strain are capable of hybridizing with segregants of compatible sex type.

The expression "region linked to" is equivalent herein to the expression "region genetically linked to".

A region linked to a sex type expression locus is a region such that the risk of a recombination by crossing-over, between said region and said sex type expression locus, during meiosis, is very low.

As a result, by integrating the gene integration cassette into a region linked to a sex type expression locus, the expression cassette(s) of said gene integration cassette and said sex type expression locus have strong chances of segregating together during meiosis, i.e. of being in the same segregant.

A recombination sequence preferably consists of at least 15 base pairs, more preferentially at least 20 base pairs, more preferentially at least 50 base pairs, even more preferentially at least 100 base pairs and even more preferentially at least 200 base pairs.

A recombination sequence consists, for example, of 200 to 400 base pairs.

An object of the present invention is also a gene integration cassette comprising:
- at least two expression cassettes, each cassette comprising a gene of interest framed by a promoter and a terminator,
- two recombination sequences which are homologs of a region linked to a sex type expression locus and which frame said expression cassettes.

An object of the present invention is particularly a gene integration cassette as defined above, characterized in that said region linked to a sex type expression locus is a region located less than 5 cM from said sex type expression locus.

The expression "region located less than 5 cM from the sex type expression locus" is intended to mean a region located less than 5 cM from either side of the sex type expression locus.

The centimorgan, denoted cM, is the unit of measurement of the distance between two genetically linked genes.

The centimorgan is defined as the frequency of recombination, during meiosis, between two genes of which the loci are on the same chromosome and of which the alleles present on each chromosome define, for each of them, a haplotype.

Therefore, a region located less than 5 cM from the sex type expression locus signifies that the frequency of recombination between said region and said sex type expression locus is 5%, i.e. 5 crossing-over events on average of this distance for 100 meioses.

An object of the present invention is also a gene integration cassette as defined above, characterized in that said region linked to a sex type expression locus is a region located less than 4 cM, preferably less than 3 cM, more preferentially less than 2 cM and even more preferentially less than 1 cM from said sex type expression locus.

An object of the present invention is particularly a gene integration cassette as defined above, characterized in that said region linked to a sex type expression locus is a region located less than 10 500 base pairs from said sex type expression locus.

The expression "region located less than 10 500 base pairs from the sex type expression locus" is intended to mean a region located less than 10 500 base pairs from either side of the sex type expression locus.

For example, the gene integration cassette as defined above is characterized in that said region linked to a sex type expression locus is a region located less than 10 500 base pairs from the MAT locus of *Saccharomyces cerevisiae*.

An object of the invention is also a gene integration cassette as defined above, characterized in that said region linked to a sex type expression locus is a region located less than 8500 base pairs, preferably less than 6500 pairs, more preferentially less than 4500 base pairs and even more preferentially less than 2500 base pairs from said sex type expression locus.

The gene integration cassette preferably comprises at least one selectable marker, in order to allow the selection of the yeast cells which have integrated said integration cassette.

In one preferred embodiment, improved strains of yeast according to the invention do not comprise a selectable marker.

The cre-lox system can then be used in order to easily remove the selectable marker(s) used in the gene integration cassette, while at the same time leaving in the genome of the yeast strain only a scar comprising a lox sequence.

An object of the present invention is thus a gene integration cassette as defined above, comprising, between said two recombination sequences, two lox sequences framing an expression cassette, said expression cassette comprising a selectable marker framed by a promoter and a terminator.

The gene integration cassette according to the invention comprises, for example:

- at least two expression cassettes, each expression cassette comprising a gene of interest framed by a promoter and a terminator,
- two lox sequences framing an expression cassette, said expression cassette comprising a selectable marker framed by a promoter and a terminator,
- two recombination sequences which are homologs of a region linked to a sex type expression locus and which frame said expression cassettes and said two lox sequences.

The expression cassettes comprising the genes of interest and the expression cassette comprising the selectable marker which is framed by the lox sequences are placed in any desired order on the inside of the recombination sequences.

Figure 1:
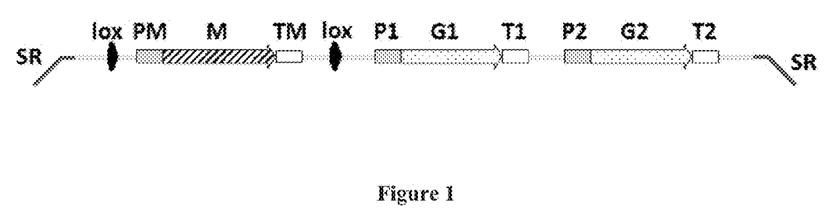
FIG. 1: Diagram of a gene integration cassette comprising:
two expression cassettes, each expression cassette comprising a gene of interest (respectively G1 and G2) framed by a promoter P (respectively P1 and P2) and a terminator (respectively T1 and T2).
two lox sequences which frame an expression cassette, said expression cassette comprising a selectable marker (M) framed by a promoter (PM) and a terminator (TM).
two recombination sequences (SR) which are homologs of a region linked to a sex type expression locus and which frame said two expression cassettes and said two lox sequences.

An example of a gene integration cassette is given in FIG. 1.

The selectable marker is preferably a dominant selectable marker.

A dominant selectable marker is a gene of which a single functional copy is sufficient to allow the cell to multiply on a selective medium.

The dominant selectable marker is, for example, a gene for resistance to an antibiotic, a gene encoding an exogenous enzyme which has a polysaccharide-hydrolyzing activity, or a gene encoding an acetamidase.

The gene encoding an exogenous enzyme which has a polysaccharide-hydrolyzing activity is, for example, a gene encoding an enzyme which has a melibiase activity, an alpha-amylase activity or an isomaltase activity.

The gene for resistance to an antibiotic is, for example, chosen from the gene for resistance to kanamycin, blasticidin, phleomycin, hygromycin or nourseothricin.

The two lox sequences make it possible to excise the selectable marker by using a Cre recombinase.

The two lox sequences have, for example, the following loxP sequence of 34 base pairs:

(SEQ ID NO: 1)
ATAACTTCGTATAATGTATGCTATACGAAGTTAT.

An object of the present invention is also a gene integration cassette as defined above, comprising at least three expression cassettes, each expression cassette comprising a gene of interest framed by a promoter and a terminator.

The gene integration cassette can, for example, comprise three expression cassettes, four expression cassettes, five expression cassettes, or more than five expression cassettes, each expression cassette comprising a gene of interest framed by a promoter and a terminator.

In one advantageous embodiment of the invention, the gene integration cassette as defined above is characterized in that said region linked to a sex type expression locus comprises the BUD5 gene, the TAF2 gene and/or the sex type expression locus.

In one particularly advantageous embodiment, the gene integration cassette as defined above is characterized in that said region linked to a sex type expression locus is located in the BUD5 gene, in the TAF2 gene and/or in the sex type expression locus.

An object of the present invention is thus also a gene integration cassette as defined above, characterized in that the recombination sequences are homologs of a region included in the BUD5 gene, in the TAF2 gene and/or in the sex type expression locus.

The BUD5 gene is also referenced under number YCR038C.

The BUD5 gene has already been used by the applicant as a gene integration site, since it is a region which has been found to be very favorable to the expression of a reporter gene by exhibiting a high level of beta-glucosidase activity in the yeast cells thus transformed (cf. Yamane et al., *J. Gen. Appl. Microbiol*, 1998, 44, 275-281). Thus, the region of the genome corresponding to the BUD5 gene was used only for the purpose of obtaining a strong expression of the integrated gene.

The TAF2 gene is also referenced under number YCR042C.

One of the recombination sequences may, for example, be a homolog of the 3' end or of the 5' end of the sex expression locus.

One recombination sequence is, for example, a homolog of a region comprised in the BUD5 gene or in the TAF2 gene, and the other recombination sequence is, for example, a homolog of a region comprised in the sex type expression locus.

In another example, the two recombination sequences are homologs of a region located in the BUD5 gene or of a region included in the TAF2 gene.

One recombination sequence may also be a homolog of a region overlapping the BUD5 gene and the sex type expression locus, or else of a region overlapping the TAF2 gene and the sex type expression locus.

In one preferred embodiment of the invention, one recombination sequence is a homolog of the BUD5 gene and the other recombination sequence is a homolog of the MAT locus.

For example, one recombination sequence is a homolog of the *Saccharomyces* BUD5 gene, preferably of the 5' region of the BUD5 gene, and the other recombination sequence is a homolog of the *Saccharomyces* alpha2 gene, preferably of the 3' region of the alpha2 gene.

An object of the present invention is also a vector comprising a gene integration cassette as defined above.

The term "vector" denotes herein a DNA molecule capable of self-replication in *E. coli*.

A vector is, for example, chosen from a plasmid, a cosmid, a bacterial artificial chromosome, also known as BAC, a P1 bacteriophase-derived artificial chromosome, also known as PAC, and a virus-derived vector.

An object of the present invention is also a yeast strain comprising at least two genes of interest integrated into a region linked to the same-sex-type expression locus.

Such a yeast strain constitutes an intermediate product of the implementation of the method for obtaining improved strains of yeast according to the invention.

The yeast strain comprising at least two genes of interest integrated into a region linked to the same-sex-type expression locus is heterozygous at the level of the sex type expression locus. i.e. it has at least one allele of each of the sex types.

The yeast strain comprising at least two genes of interest integrated into a region linked to the same-sex-type expression locus is a haplodiplontic yeast strain.

A haplodiplontic yeast strain which can be used in the context of the invention is as defined above.

A haplodiplontic yeast strain which is preferred according to the invention is a *Saccharomyces* strain, preferably a *Saccharomyces cerevisiae* strain.

The sex type expression locus is as defined above.

The genes of interest are integrated into a region linked to the same-sex-type expression locus, i.e. same-allele expression locus.

In the case of a *Saccharomyces* strain, the genes of interest are integrated into a region linked to the same-sex-type MAT locus, i.e. to the MATa-type MAT locus or to the MATalpha-type MAT locus.

An object of the present invention is also a yeast strain comprising at least three genes of interest, for example three genes of interest, four genes of interest, five genes of interest, or more than five genes of interest.

An object of the present invention is particularly a yeast strain as defined above, comprising at least two genes of interest integrated into a region linked to a same-sex-type expression locus, transformed with a gene integration cassette as defined above or with a vector as defined above.

An object of the present invention is also a method for obtaining an improved strain of yeast, by integrating at least one gene into a yeast strain, and then crossing said yeast strain thus obtained with another yeast strain.

As indicated above, the method according to the invention is fast, efficient and simple to carry out. In particular, the method according to the invention makes it possible to improve the efficiency and therefore to reduce the duration of the step of selecting the segregants resulting from each yeast strain used in the crossing, even by integrating a single gene.

An object of the present invention is a method for obtaining an improved strain of yeast by integrating at least one gene of interest and then crossing, comprising the steps of:
  selecting a yeast strain X which is heterothallic and heterozygous at the level of the sex type expression locus,
  integrating, in the genome of said yeast strain X, at least one gene of interest into a region linked to a sex type expression locus, so as to obtain a genetically modified yeast strain X,
  crossing the genetically modified yeast strain X with a yeast strain Y, so as to obtain a hybrid.

The method according to the invention is applicable to any haplodiplontic yeast strain X.

A haplodiplontic yeast strain which can be used in the context of the invention is as defined above.

A haplodiplontic yeast strain which is preferred according to the invention is a *Saccharomyces* strain, preferably a *Saccharomyces cerevisiae* strain.

The sex type expression locus is as defined above.

The yeast strain X is heterozygous at the level of the sex type expression locus, i.e. it has at least one allele of each of the sex types.

For example, in the case of a *Saccharomyces* strain, the yeast strain X has at least one MATalpha allele and at least one MATa allele.

A heterothallic yeast strain is a yeast strain of which the sex type is intrinsically stable.

In particular, a heterothallic *Saccharomyces* strain is a yeast strain which does not have endonuclease activity.

A yeast strain which does not have Ho endonuclease activity is described as being of Ho-genotype.

The activity of an Ho endonuclease can in fact enable the sex type to be changed, by changing the genetic composition of the sex type locus.

The integrating step is preferably carried out using a gene integration cassette as defined above, for example by means of a vector as defined above.

The integrating step can comprise the integration, in the genome of the yeast strain X, of at least two genes of interest into a region linked to the same-sex-type expression locus, so as to obtain a genetically modified yeast strain X.

The integrating step can also comprise the integration, in the genome of the yeast strain X, of at least three genes of interest into a region linked to the same-sex-type expression locus, for example three genes of interest, four genes of interest, five genes of interest, or more than five genes of interest, so as to obtain a genetically modified yeast strain X.

In the case of a *Saccharomyces* strain, the genes of interest are integrated into a region linked to the same-sex-type MAT locus, i.e. either of the MATa type or of the MATalpha type.

When at least two genes of interest are integrated, they can be integrated using several gene integration cassettes, for example one integration cassette for each gene or for several genes, or using one gene integration cassette comprising all the genes of interest.

Thus, all the genes of interest are integrated into a region linked to the same-sex-type expression locus, but they are not necessarily integrated at the same place in the genome of the yeast strain.

The genetically modified yeast strain X is crossed with a yeast strain Y, so as to obtain a hybrid.

The hybrid corresponds to the improved strain of yeast according to the invention.

The yeast strain Y is also a haplodiplontic yeast strain.

The yeast strain Y is preferably of the same genus, preferably the same species as the yeast strain X.

In one particular embodiment, the genetically modified yeast strain X is crossed with the nonmodified yeast strain X. In this case, the nonmodified yeast strain X and the yeast strain Y are identical.

Thus, the segregants resulting from the sporulation of the yeast strain X can be easily selected, in a single step, with respect to the sex type corresponding to the integration of the genes.

Indeed, there is no need to evaluate both the sex type of the segregant of the yeast strain X, and the presence of the gene(s) of interest.

The determination of the sex type of a segregant is carried out using the techniques well known to those skilled in the art, for example by PCR or else by crossing with a haploid yeast strain of known sex type (obtaining a diploid indicates that the starting segregant is of the compatible sex type).

Next, the step of selecting the segregants of the yeast strain Y is highly simplified, since only the segregants of the sex type compatible with the segregant X are analyzed.

The method according to the invention therefore exhibits advantages from the moment there is integration of a gene of interest.

The method according to the invention is even more advantageous when using two genes of interest, since, in addition to what is previously indicated:
  the genes of interest of the yeast strain X all segregate in the segregant of the sex type corresponding to the integration of said genes, instead of being randomly distributed between each segregant, thereby significantly increasing the chances of obtaining segregants which comprise all the genes of interest, and the selection of the segregants of the yeast strain X is greatly simplified, since it is possible to select, in a single step, the segregants of the sex type corresponding to the integration of all the genes of interest.

An object of the present invention is particularly the method as defined above, characterized in that the genetically modified yeast strain X is a yeast strain as defined above, comprising at least two genes of interest integrated into a region linked to a same-sex-type expression locus, preferably transformed with an integration cassette as defined above or with a vector as defined above.

The crossing step is carried out according to the conventional techniques, such as those taught in chapter 7 "Sporulation and Hybridization of Yeast" by R. R. Fowell, of the reference book "The Yeasts", Volume 1, edited by A. H. Rose and J. S. Harrison, 1969—Academic Press.

An object of the present invention is thus a method as defined above, characterized in that the step of crossing the genetically modified yeast strain X with a yeast strain Y comprises the steps of:

a) sporulation of the genetically modified yeast strain X and selection of at least one segregant of the sex type corresponding to the integration of said gene(s) of interest, so as to obtain at least one segregant X, b) sporulation of the yeast strain Y and selection of at least one segregant of the yeast strain Y of sex type compatible with the segregant X, so as to obtain a segregant Y, c) hybridization of at least one segregant X with at least one segregant Y, so as to obtain at least one hybrid.

An object of the present invention is also a method as defined above, characterized in that the yeast strain Y comprises at least one gene of interest integrated into a region linked to a sex type expression locus.

The yeast strain Y can comprise at least two genes of interest, for example two genes of interest, three genes of interest, four genes of interest, five genes of interest, or more than five genes of interest.

In one advantageous embodiment, the gene(s) of interest of the yeast strain Y is (are) integrated into a region linked to a sex type expression locus compatible with the sex type of the segregant X.

In another advantageous embodiment, the gene(s) of interest of the yeast strain Y is (are) integrated into a region linked to an expression locus of the same sex type as that of the segregant X.

In such a case, in order to obtain a segregant Y comprising said gene(s) of interest of the yeast strain Y which is of sex type compatible with a segregant X comprising said gene(s) of interest of the yeast strain X, it is possible to change the sex type of the sex expression locus corresponding to the integration of said gene(s) of interest of the yeast strain X or of the yeast strain Y, according to the techniques well known to those skilled in the art, for example using a plasmid containing the HO gene which would express the HO endonuclease in the yeast strain (cf. Herskowitz, I. and Jensen R. E., 1991, Methods Enzymol 194, 132-46).

The segregants resulting from the sporulation of the yeast strain Y comprising at least one gene of interest can be easily selected, in a single step, with respect to the sex type corresponding to the integration of the gene(s) of interest.

According to one particular embodiment, the method according to the invention comprises crossing a yeast strain X comprising one or more genes of interest with a yeast strain Y which exhibits at least one characteristic of interest.

An object of the present invention is thus quite particularly a method as defined above, characterized in that the yeast strain Y has at least one characteristic of interest.

A characteristic of interest within the meaning of the invention is genetically transmissible. The characteristic of interest may be dominant or co-dominant.

A dominant characteristic of interest is a characteristic which is transmissible in a single generation.

A characteristic of co-dominant interest is a characteristic which is partially transmissible in a single generation.

Examples of a characteristic of interest are:

resistance and/or tolerance to a stress and/or to an inhibitor, such as osmotic pressure, pH, the presence of organic acids, a high alcohol concentration, the presence of aromatic compounds such as terpenes, an antibiotic, a high temperature, freezing, drying, and a combination thereof, and/or a high ethanol yield in fermentation and/or a high fermentative capacity in breadmaking and/or a high biomass production yield.

The invention cannot be limited to the characteristics of interest indicated above.

An object of the present invention is particularly a method as defined above, characterized in that the crossing step b) also comprises selecting a segregant of the yeast strain Y which has all or part of said characteristic of interest, so as to obtain a segregant Y.

An object of the present invention is also a method as defined above, characterized in that it comprises a subsequent step of selecting at least one hybrid which has all or part of the characteristic of interest of the yeast strain Y.

The yeast strain X can also have at least one characteristic of interest.

In this case, the segregants which have all or part of the characteristic of interest of the yeast strain X are selected from the segregants of the yeast strain X of the sex type corresponding to the integration of the gene(s) of interest.

An object of the present invention is also a method as defined above, characterized in that it comprises a subsequent step of selecting at least one hybrid which has all or part of the characteristic of interest of the yeast strain X.

An object of the present invention is particularly an improved strain of yeast which can be obtained by means of the method as defined above.

An object of the present invention is also a yeast strain derived from an improved strain of yeast as defined above, said derived strain of yeast comprising said gene(s) of interest of the yeast strain X.

The expression "derived strain" denotes a strain derived via one or more crosses and/or via mutation and/or via genetic transformation.

A strain derived via crossing can be obtained by crossing a strain according to the invention with the same strain, or another strain according to the invention, or any other strain.

A strain derived via mutation can be a strain which has undergone at least one spontaneous mutation in its genome or at least one mutagenesis-induced mutation. The mutation(s) of a derived strain may or may not be silent.

The expression "mutagenesis" denotes both random mutagenesis obtained by applying radiation (for example UV radiation), or using mutagenic chemical agents, and insertional or site-directed mutagenesis, by transposition or by integration of an exogenous DNA fragment. A strain derived via genetic transformation is a strain into which has been introduced a DNA sequence which is preferably provided by a plasmid or directly integrated into the genome.

An object of the present invention is also a yeast obtained by culturing an improved strain of yeast as defined above or a derived strain of yeast as defined above.

The yeasts are produced from broad-spectrum yeast strains according to the invention, in particular as described in the reference book "Yeast Technology", $2^{nd}$ edition, 1991, G. Reed and T. W. Nagodawithana, published by Van Nostrand Reinhold, ISBN 0-442-31892-8.

The industrial-scale multiplication of yeasts generally comprises at least the first two steps of the set of the following steps:
- multiplying a yeast strain in several stages, first under semi-anaerobic conditions and then under aerobic conditions,
- separating the yeast thus produced, from its culture medium, by centrifugation, so as to obtain a liquid cream yeast containing approximately between 12% and 25% of dry matter, or even a higher amount of dry matter if the cream yeast is mixed with osmolyte products,
- filtering the resulting liquid cream yeast, generally on a rotary filter under vacuum, so as to obtain a dehydrated fresh yeast containing from 26% to 35% of dry matter.
- mixing said dehydrated fresh yeast, so as to obtain a homogeneous mass,
- extruding the resulting yeast, so as to obtain:
  - a pressed yeast in the form of fresh yeast cakes or of crumbled fresh yeast, containing approximately 30% of dry matter, or
  - a yeast in the form of particles, generally of granules, if the yeast is intended to be dried,
- optionally, drying in a sparing manner, in a stream of hot air, for example by fluidization, of the yeast particles obtained by extrusion, so as to obtain dry yeast.

An object of the present invention is also the use of a region linked to a sex type expression locus, for integrating at least one gene of interest into a yeast strain intended to be crossed with a yeast strain.

The sex type expression locus is as defined above.

An object of the present invention is the use as defined above, in which the yeast strain into which at least one gene of interest is integrated is a haplodiplontic yeast strain, for example as defined above.

A haplodiplontic yeast strain which is preferred according to the invention is a *Saccharomyces* strain, preferably a *Saccharomyces cerevisiae* strain.

An object of the present invention is the use as defined above, in which the yeast strain into which at least one gene of interest is integrated is intended to be crossed with another yeast strain, or the same yeast strain before the integration of the gene(s) of interest.

An object of the present invention is the use as defined above, in which the yeast strain into which at least one gene of interest is integrated is intended to be crossed with a yeast strain which also comprises at least one gene of interest integrated into a region linked to the sex type expression locus.

An object of the present invention is the use as defined above, in which the yeast strain into which at least one gene of interest is integrated is heterozygous at the level of the sex type expression locus, i.e. it has at least one allele of each of the sex types.

An object of the present invention is the use as defined above of a region linked to a sex type expression locus, for integrating at least two genes of interest into a yeast strain intended to be crossed with a yeast strain, preferably at least three genes of interest, for example three genes of interest, four genes of interest, five genes of interest, or more than five genes of interest.

An object of the present invention is the use as defined above, in which said region linked to a sex type expression locus is a region located less than 5 cM, preferably less than 4 cM, preferably less than 3 cM from said sex type expression locus, more preferentially less than 2 cM, even more preferentially less than 1 cM.

An object of the present invention is the use as defined above, in which said region linked to a sex type expression locus is a region located less than 10 500 base pairs, preferably less than 8500 base pairs, preferably less than 6500 base pairs, more preferentially less than 4500 base pairs and even more preferentially less than 2500 base pairs from said sex type expression locus.

Other characteristics and advantages of the invention will emerge even more clearly on reading the following exemplary embodiment which illustrates the invention without limiting it.

EXAMPLE

Obtaining an Improved Yeast Strain by Crossing a Genetically Modified Yeast Strain with Another Yeast Strain Materials and Methods
(i) Yeast Production The yeast production was carried out in the manner described in the handbook "Yeast technology", $2^{nd}$ edition, 1991. G. Reed and T. W. Nagodawithana, published by Van Nostrand Reinhold, ISBN 0-442-31892-8, in particular by carrying out two successive precultures followed by a fed-batch culture. The resulting yeast was then dried so as to obtain a dry yeast.

(ii) Measurement of Fermentative Capacity

The fermentative capacity of a yeast corresponds to the volume of $CO_2$ (in ml) produced by the yeast in fermentation in a dough.

The fermentative capacity of the yeasts was measured on dry yeast, in a sugar-free dough containing 20 g of flour.

The dry yeast, in an amount equal to 160 mg of dry matter, was rehydrated in 6 ml of distilled water at 38° C. for 15 minutes. 9 ml of a mixture of water and 405 mg of NaCl were then added. A suspension of yeasts in an aqueous solution containing 27 g/l of NaCl was thus obtained.

The flour and said suspension of yeasts were kneaded for 40 seconds in a kneading machine, so as to obtain a dough which was then placed in a container which was placed in a water bath at 30° C. 13 minutes after the beginning of the kneading, the container containing the dough was hermetically closed.

The volume of gas given off was measured during the $1^{st}$ hour and during the $2^{nd}$ hour, by means of a Risograph (National Manufacturing, Lincoln. Nebr.). The total volume in ml over the course of 2 hours at 30° C. was then indicated.

(iii) Preparation of the Genetically Modified Yeast Strain X

The yeast strain X was a *Saccharomyces cerevisiae* strain which has been genetically modified so as to be able to multiply, under aerobic conditions, in a culture medium containing a mixture of glycerol and sugar, by consuming the glycerol.

Figure 2:
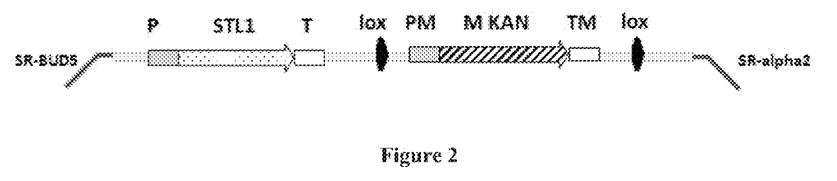
FIG. 2: Diagram of the expression cassette used in Example 1 for integrating the STL1 gene into the genome of the yeast strain.

To this effect, the STL1 gene was integrated into a region included between the 5' end of the BUD5 gene and the 3' end of the alpha2 gene (located in the MATalpha locus) using the gene integration cassette represented in FIG. 2.

The STL1 gene was under the control of the pADH1 promoter and the terminator is tCYC1.

The integration cassette comprised the kanamycin selectable marker, conferring geneticin resistance, framed by a promoter and by a terminator and by two loxP sequences.

The first recombination sequence was a homolog of a region included in the first 600 base pairs of the BUD5 gene and the second recombination sequence was a homolog of a region included from base pair 150 to the end of the alpha2 gene.

The selectable marker was used to select the yeast strains which have integrated the STL1 gene.

The integration of the STL1 gene at the level of the BUD5 gene and of the alpha2 gene was verified.

The selectable marker was then excised using the Cre recombinase.

The resulting yeast strain corresponded to the yeast strain F.

(iv) Crossing

The starting yeast strain F was crossed with the starting yeast strain G.

The yeast strain G was a *Saccharomyces cerevisiae* strain which is effective in breadmaking on sugar-free dough.

In particular, the yeast strain G gives yeasts which have a fermentative capacity greater than or equal to 150 ml in sugar-free dough.

Step 1:
Growth of the Yeast Strain

A loop of the starting strain (stored at −80° C.) was inoculated at the surface of the agar of a Petri dish of medium A.

The composition of the medium A was as follows: 10 g of yeast extract, 10 g of peptone, 20 g of glucose, 20 g of agar, pH 6.2+/−0.2, water qs 1 l.

The Petri dish was then incubated for 24 hours at 30° C.

Step 2:
Sporulation on Medium 2

A loop of the previous culture was inoculated at the surface of the agar of a Petri dish of medium B.

The composition of the medium B was as follows: 6.5 g of sodium acetate, 15 g of agar, pH 6.5-7, water qs 1 l.

The Petri dish was incubated for 96 hours at 25° C. The biomass obtained at the surface of the dish was then harvested in 500 µl of sterile water. 25 µl of zymolyase were added to 100 µl of this suspension. The suspension was incubated for 30 minutes at 30° C., before being plated out on an agar dish of medium 1. The tetrads were preferably dissected 20 minutes later.

Step 3:
Tetrad Dissection

The tetrads were dissected with a Singer micromanipulator, then the Petri dish was incubated for 48 hours at 30° C.

Step 4:
Segregant Storage

The segregants were then stored at −80° C. in medium 1 containing 20% of glycerol.

Step 5:
Selection of the Segregants of the Yeast Strain F

The segregants of the yeast strain F were selected on the basis of the presence of the MATalpha allele which reflects a ploidy level compatible with a subsequent hybridization and corresponds to the segregants having integrated the STL1 gene.

The presence of the MATalpha allele was determined by PCR. This reaction was carried out using the genomic DNA of each potential segregant as template. The oligonucleotides were a primer specific to the MAT locus expressed on chromosome III of the yeast (Mat1 primer) and two other primers, one specific to MATalpha (Mat2 primer) and the other specific to MATa (Mat3 primer). The MATalpha genotype of the yeast cells was characterized by the presence of an amplicon of 404 base pairs detectable on a 0.8% agarose gel.

The Mat1 primer has the following sequence SEQ ID NO: 2:

AGTCACATCAAGATCGTTTATGG.

The Mat2 primer has the following sequence SEQ ID NO: 3:

GCACGGAATATGGGACTACTTCG.

The Mat3 primer has the following sequence SEQ ID NO: 4:

ACTCCACTTCAAGTAAGAGTTTG.

Step 6:
Selection of the Segregants of the Yeast Strain G

The segregants of the yeast strain G were selected according to two criteria. The first was the presence of the MATa allele which reflects a ploidy level compatible with a subsequent hybridization with the segregant of the yeast strain F. The second criterion was fermentative capacity of these segregants.

The presence of the MATa allele was determined by PCR. This reaction was carried out using the genomic DNA of each potential segregant as template. The oligonucleotides were a primer specific to the MAT locus expressed on chromosome III of the yeast (Mat1 primer of sequence SEQ ID NO: 2) and two other primers, one specific to MATalpha (Mat2 primer of sequence SEQ ID NO: 3) and the other specific to MATa (Mat3 primer of sequence SEQ ID NO: 4).

The genotype MATa of the yeasts was characterized by the presence of an amplicon of 544 base pairs detectable on a 0.8% agarose gel.

The fermentative capacity of the segregants was determined as described above.

The segregants having a fermentative capacity greater than 100 ml were selected.

Step 7:
Crossing and Selection of Hybrids

A loop of a MATalpha haploid segregant was inoculated at the surface of the agar of a Petri dish of medium A. A loop of a MATa haploid segregant was mixed with the deposit of the MATalpha segregant.

The composition of the medium A was as follows: 10 g of yeast extract, 10 g of peptone, 20 g of glucose, 20 g of agar, pH 6.2+/−0.2, water qs 1 l.

The Petri dish was then incubated for 24 hours at 30° C. A loop of the mixture was inoculated at the surface of the agar of a Petri dish of medium A. This step was repeated 5 times. During the final inoculation, the cells were streaked so as to obtain isolated colonies, each corresponding to a yeast strain.

On each isolation, the yeast cells were cultured so as to be able to extract the genomic DNA therefrom, and then a PCR was carried out so as to verify that, in the same cell, the MATa and MATalpha alleles were indeed present. This reaction was carried out using the genomic DNA of each potential hybrid as template.

The oligonucleotides were a primer specific to the MAT locus expressed on chromosome III of the yeast (Mat1 primer of sequence SEQ ID NO: 2) and two other primers, one specific to MATalpha (Mat2 of sequence SEQ ID NO: 3) and the other specific to MATa (Mat3 of sequence SEQ ID NO: 4). The MATalpha/a genotype of the yeast strains was characterized by the presence of two amplicons of 404 and 544 base pairs detectable on a 0.8% agarose gel.

The capacity of the resulting yeast strains to multiply, under aerobic conditions, in a culture medium comprising a mixture of glycerol and sugar, so as to obtain yeasts, and then the fermentative capacity of the resulting yeasts in sugar-free dough, were then evaluated.

Results

The objective of this example was to obtain an improved yeast strain capable of multiplying under aerobic conditions in a medium containing glycerol and glucose, by consuming the glycerol, and giving yeasts which have a fermentative capacity that enables their use in breadmaking.

The starting strain F was a *Saccharomyces cerevisiae* strain which has been genetically modified by integrating the STL1 gene into a region linked to the MAT locus of MATalpha sex type.

This simple genetic modification allowed the starting strain F to multiply, under aerobic conditions, in a culture medium containing glycerol and sugar, by consuming the glycerol.

After sporulation, the MATalpha sex type segregants of the yeast strain F were selected by PCR.

In order to improve the breadmaking performance levels of the yeast strain F, it was crossed with a starting strain G which is a *Saccharomyces cerevisiae* strain which has not been genetically modified and which gives yeasts which are effective in breadmaking on sugar-free doughs.

After sporulation of the starting strain G. MATa sex type segregants were selected by PCR, and then a second selection was carried out among these MATa sex type segregants on the basis of their fermentative capacity.

The selected segregants of the yeast strain F and of the yeast strain G were then hybridized.

Thus, the method used is fast, simple to carry out and efficient:
- the MATalpha segregants of the yeast strain F were selected in a single step, without needing to verify both the presence of the STL1 gene and the sex type of the segregant,
- only the fermentative capacities of the MATa sex type segregants of the yeast strain G were evaluated, instead of evaluating the fermentative capacity of all the segregants resulting from the yeast strain G.

The invention claimed is:

1. A gene integration cassette for the integration of genes into the genome of a yeast strain, comprising:
    at least two expression cassettes, each expression cassette comprising a gene of interest framed by a promoter and a terminator,
    two recombination sequences which are homologs of a region linked to a sex type expression locus and which frame said expression cassettes,
    wherein said region linked to a sex type expression locus is a region located at least 5 cM from said sex type expression locus.

2. The gene integration cassette as claimed in claim 1, wherein said region linked to a sex type expression locus is a region located less than 10 500 base pairs from said sex type expression locus.

3. The gene integration cassette as claimed in claim 1, further comprising, between said two recombination sequences, two lox sequences framing an expression cassette, wherein said expression cassette comprises a selectable marker framed by a promoter and a terminator.

4. The gene integration cassette as claimed in claim 1, characterized in that said region linked to a sex type expression locus is located in at least one of: the BUD5 gene, the TAF2 gene and the sex type expression locus.

5. A vector comprising a gene integration cassette as claimed in claim 1.

6. A yeast strain comprising at least two genes of interest integrated into a region linked to the same-sex-type expression locus, which can be obtained by transformation using a gene integration cassette as claimed in claim 1.

7. A method for obtaining an improved strain of yeast by integrating at least two genes of interest and crossing, comprising steps of:
    selecting a yeast strain X which is heterothallic and heterozygous at the level of the sex type expression locus,
    integrating, in the genome of said yeast strain X, at least two genes of interest into a region linked to a sex type expression locus, so as to obtain a genetically modified yeast strain X that comprises the at least two genes of interest integrated into the region linked to the sex type expression locus, and
    crossing the genetically modified yeast strain X with a yeast strain Y, so as to obtain a hybrid.

8. The method as claimed in claim 7, wherein the step of crossing the genetically modified yeast strain X with a yeast strain Y comprises steps of:
    a) performing a sporulation of the genetically modified yeast strain X and selecting at least one segregant of the sex type corresponding to the integration of said gene (s) of interest, so as to obtain at least one segregant X,
    b) performing a sporulation of the yeast strain Y and selecting at least one segregant of the yeast strain Y of sex type compatible with the segregant X, so as to obtain a segregant Y, and
    c) hybridizing at least one segregant X with at least one segregant Y, so as to obtain at least one hybrid.

9. The method as claimed in claim 7, wherein the yeast strain Y comprises at least one gene of interest integrated into a region linked to a sex type expression locus.

10. The method as claimed in claim 7, wherein the yeast strain Y has at least one characteristic of interest.

11. The method as claimed in claim 8, wherein the yeast strain Y has at least one characteristic of interest and wherein step b) also comprises selecting a segregant of the yeast strain Y which has all or part of said characteristic of interest, so as to obtain a segregant Y.

12. The method as claimed in claim 10, further comprising a subsequent step of selecting at least one hybrid which has all or part of said characteristic of interest of the yeast strain Y.

13. The gene integration cassette as claimed in claim 2, further comprising, between said two recombination sequences, two lox sequences framing an expression cassette, wherein said expression cassette comprises a selectable marker framed by a promoter and a terminator.

14. The gene integration cassette as claimed in claim 2, characterized in that said region linked to a sex type expression locus is located in at least one of: the BUD5 gene, the TAF2 gene and the sex type expression locus.

15. The gene integration cassette as claimed in claim 3, characterized in that said region linked to a sex type expression locus is located in at least one of: the BUD5 gene, the TAF2 gene and the sex type expression locus.

16. A yeast strain comprising at least two genes of interest integrated into a region linked to the same-sex-type expression locus, which can be obtained using a vector as claimed in claim 5.

17. The method as claimed in claim 8, wherein the yeast strain Y comprises at least one gene of interest integrated into a region linked to a sex type expression locus.

18. The method as claimed in claim 11, further comprising a subsequent step of selecting at least one hybrid which has all or part of said characteristic of interest of the yeast strain Y.

19. An improved yeast strain obtained by:
    selecting a yeast strain X which is heterothallic and heterozygous at the level of the sex type expression locus;
    integrating, in the genome of said yeast strain X, at least two genes of interest into a region linked to a sex type expression locus, so as to obtain a genetically modified yeast strain X that comprises the at least two genes of interest integrated into the region linked to the sex type expression locus; and
    crossing the genetically modified yeast strain X with a yeast strain Y, so as to obtain a hybrid
    wherein the improved yeast strain is a hybrid that comprises the at least two genes of interest integrated into the region linked to the sex type expression locus, wherein said region linked to the sex type expression locus is a region located at less than 5 cM from said sex type expression locus.

20. The improved yeast strain according to claim 19, wherein crossing the genetically modified yeast strain X with a yeast strain Y comprises steps of:
    a) performing a sporulation of the genetically modified yeast strain X and selecting at least one segregant of the sex type corresponding to the integration of said at least two genes of interest, so as to obtain at least one segregant X,
    b) performing a sporulation of the yeast strain Y and selecting at least one segregant of the yeast strain Y of sex type compatible with the segregant X, so as to obtain a segregant Y, and
    c) hybridizing at least one segregant X with at least one segregant Y, so as to obtain at least one hybrid.

21. The improved yeast strain according to claim 19, wherein the yeast strain Y comprises at least one gene of interest integrated into a region linked to a sex type expression locus.

22. The improved yeast strain according to claim 19, wherein the yeast strain Y has at least one characteristic of interest, wherein the at least one characteristic of interest is selected from the group consisting of resistance to a stress and/or inhibitor, tolerance to a stress and/or inhibitor, high ethanol yield in fermentation, high fermentative capacity in breadmaking, high biomass production yield, and any combination thereof.

23. The improved yeast strain according to claim 22, wherein at least one hybrid is selected which has all or part of said characteristic of interest of the yeast strain Y.

24. The improved yeast strain according to claim 20, wherein the yeast strain Y has at least one characteristic of interest, wherein the at least one characteristic of interest is selected from the group consisting of resistance to a stress and/or inhibitor, tolerance to a stress and/or inhibitor, high ethanol yield in fermentation, high fermentative capacity in breadmaking, high biomass production yield, and any combination thereof, and wherein step b) also comprises selecting a segregant of the yeast strain Y which has all or part of said characteristic of interest, so as to obtain a segregant Y.

25. A yeast strain derived from an improved strain of yeast as claimed in claim 19, wherein said derived strain of yeast comprises said at least two genes of interest of the yeast strain X.

26. A yeast obtained by culturing an improved strain of yeast as claimed in claim 19.

27. A yeast obtained by culturing a derived strain of yeast as claimed in claim 25.

28. The improved yeast strain according to claim 22, wherein the stress and/or inhibitor is selected from the group consisting of osmotic pressure, pH, presence of organic acids, high alcohol concentration, presence of aromatic compounds, presence of an antibiotic, high temperature, freezing, drying, and any combination thereof.

29. The improved yeast strain according to claim 24, wherein the stress and/or inhibitor is selected from the group consisting of osmotic pressure, pH, presence of organic acids, high alcohol concentration, presence of aromatic compounds, presence of an antibiotic, high temperature, freezing, drying, and any combination thereof.

* * * * *